(12) United States Patent
Rademacher et al.

(10) Patent No.: US 8,105,980 B1
(45) Date of Patent: Jan. 31, 2012

(54) METHOD OF INCREASING THE CONTENT OF FLAVONOIDS AND PHENOLIC SUBSTANCES SUBSTANCES INPLANTS

(75) Inventors: Wilhelm Rademacher, Limburgerhof (DE); Klaus Krämer, Landau (DE); Jürgen Schweden, Neustadt (DE)

(73) Assignee: Basf Aktiengesellschaft, Ludwigshafen (DE)

( * ) Notice: Subject to any disclaimer, the term of this patent is extended or adjusted under 35 U.S.C. 154(b) by 893 days.

(21) Appl. No.: 10/009,629

(22) PCT Filed: Jun. 7, 2000

(86) PCT No.: PCT/EP00/05258
§ 371 (c)(1),
(2), (4) Date: Dec. 12, 2001

(87) PCT Pub. No.: WO00/78143
PCT Pub. Date: Dec. 28, 2000

(30) Foreign Application Priority Data

Jun. 17, 1999 (DE) .................................. 199 27 571

(51) Int. Cl.
*A01N 37/00* (2006.01)
(52) U.S. Cl. .................................................. 504/307
(58) Field of Classification Search .................. 504/313, 504/307; 514/313
See application file for complete search history.

(56) References Cited

U.S. PATENT DOCUMENTS

| | | | | |
|---|---|---|---|---|
| 4,460,578 A | * | 7/1984 | Cervelle et al. | 424/757 |
| 4,866,201 A | * | 9/1989 | Motojima et al. | 560/126 |
| 5,015,283 A | * | 5/1991 | Miyazawa et al. | 504/130 |
| 6,022,831 A | * | 2/2000 | Evans | 504/313 |
| 6,099,854 A | * | 8/2000 | Howard et al. | 424/440 |
| 6,238,673 B1 | * | 5/2001 | Howard | 424/766 |

FOREIGN PATENT DOCUMENTS

| EP | 598 404 | 5/1994 |
|---|---|---|
| FR | 2727533 | 2/1999 |

OTHER PUBLICATIONS

Basak et al , Growth regulation of pome and stone fruit trees by use of prohexadione, 2000, Acta Horticulturae, 514, pp. 41-50.*
Miyazawa et al, Prohexadine-calcium, 1991, vol. 3,967-72.*
Basak et al, Grwoth regulation of pome and stone fruit trees by use of prohexadione-Ca, 1998, Acta Horticulturate, 514 (Proceedings of the XXV International Horticultural Congress, pt. 4 41-50.*
Greene, Tree growth management and fruit quality of apple trees treated with prohexadione-calcium, 1999, HortScience, vol. 34 No. 7 pp. 1209-1212.*
Ilan et al, The effect of growth retardants on anthocyanin production in carrot cell suspension cultures, Plant Cell Reports, vol. 11, No. 5-6, pp. 304-309.*
Roemmelt et al. "Effects of Prohexadione-CA on the Flavonoid Metabolism of Apple With Respect to Plant Resistance Against Fire Blight" Eight Intl Workshop on Fire Blight (1999) pp. 359-363.
Rademacher "Inhibitors of gibberellin biosynthesis: Prohexadione-Ca, a new plant growth regulator for apple with interesting biochemical features" RIKEN Review No. 21 (1999) pp. 11-12.
Rademacher, Inhibitors of gibberellin biosynthesis: Prohexadiono-Ca, a new plant growth regulator for apple with interesting biochemical features; RIKEN Review No. 21(Apr. 1999): Focused on Plant Growth Substances, pp. 11-12.

* cited by examiner

*Primary Examiner* — Alton Pryor
(74) *Attorney, Agent, or Firm* — Novak Druce + Quigg LLP (57) ABSTRACT

The invention relates to a method of increasing the flavonoid content of plants by treating the plants with the growth-regulating acylcyclohexadiones according to formula (I).

13 Claims, 4 Drawing Sheets

NF-κB -Aktivierung in Endothelzellen

1 = Endothelzellen (EC)
2 = EC + IFN-γ
3 = EC + ruhende Makrophagen (RM)
4 = EC + aktivierte Makrophagen (AM)
5 = EC + LDL + RM
6 = EC + LDL + AM
7 = EC + P-Ca (25 µg/ml) + LDL + RM
8 = EC + P-Ca (25 µg/ml) + AM
9 = EC + P-Ca (25 µg/ml) + LDL + AM

METHOD OF INCREASING THE CONTENT OF FLAVONOIDS AND PHENOLIC SUBSTANCES SUBSTANCES INPLANTS

This application is a 371 of PCT/EP00/05258 filed Jun. 7, 2000.

The present invention relates to a method of increasing the content of flavonoids and phenolic constituents in plants, wherein the plants are treated with growth-regulating acylcyclohexanediones of the formula I.

where R is, in particular, hydrogen, $C_1$-$C_6$-alkyl, $C_1$-$C_6$-haloalkyl, $C_2$-$C_{10}$-alkylthioalkyl or phenyl (substituted or unsubstituted) and R' is hydrogen, $C_1$-$C_6$-alkyl, $C_3$-$C_6$-cycloalkyl, benzyl (substituted or unsubstituted), phenylethyl, phenoxyethyl, 2-thienylmethyl, alkoxymethyl or alkylthiomethyl, and suitable salts of these compounds.

A method in which the increase is caused by treatment with acylcyclohexanediones such as prohexadione-calcium (II) and/or trinexapac-ethyl (III) is especially preferred.

The invention furthermore relates to the use of plants which have been treated by the method according to the invention with acylcyclohexanediones of the formula I, specifically prohexadione-calcium or with trinexapac-ethyl, or of parts of these plants or of products prepared with them (juices, infusions, extracts, fermentation products and fermentation residues) for the preparation of curative compositions, health-promoting compositions or tonics for humans and animals, and of cosmetics.

The invention furthermore relates to compositions prepared by the methods according to the invention wherein the grapes of red grapevines are harvested and processed whose anthocyanin production has been prevented fully or partially by treatment with acylcyclohexanediones such as prohexadione-calcium or trinexapac-ethyl and which are therefore distinguished by a qualitatively and quantitatively increased content of flavonoids and other phenolic constituents.

A variety of phenolic substances (phenylpropanoids) are found in plants, for example caffeic acid, ferulic acid, chlorogenic acid, gallic acid, eugenol, lignans, coumarins, lignin, stilbenes (polydatin, resveratrol), flavonoids (flavones, catechines, flavanones, anthocyanidines, isoflavones), polymethoxylated flavones. Accordingly, phenols are also a general component in a large number of plant-derived foodstuffs and stimulants. Certain phenolic substances are of particular importance since, after ingestion together with the food, they may exert an antioxidant effect in the human or animal metabolism (Baum, B. O.; Perun, A. L. Antioxidant efficiency versus structure. *Soc. Plast. Engrs Trans* 2: 250-257, (1962); Gardner, P. T.; McPhail, D. B.; Duthie, G. G. Electron spin resonance spectroscopic assessment of the antioxidant potential of infusions in aqueous and organic media. *J. Sci. Food Agric.* 76: 257-262, (1997); Rice-Evans, C. A.; Miller, N. J.; Pananga, G. Structure-antioxidant activity relationship of flavonoids and phenolic acids. *Free Radic. Biol. Med.* 20: 933-956, (1996); Salah, N.; Miller, N. J.; Paganga, G.; Tijburg, L.; Bolwell, G. P.; Rice-Evans, C. Polyphenolic flavonoids as scavenger of aqueous phase radicals and as chain-breaking antioxidants. *Arch Biochem Biophys* 322: 339-346, (1995); Stryer, L. *Biochemistry* S. Francisco: Freeman, (1975); Vieira, O.; Escargueil-Blanc, I.; Meilhac, O.; Basile, J. P.; Laranjinha, J.; Almeida, L.; Salvayre, R.; Negre-Salvayre, A. Effect of dietary phenolic compounds on apoptosis of human cultured endothelial cells induced by oxidized LDL. *Br J Pharmacol* 123: 565-573, (1998)). In addition, polyphenols have a multiplicity of effects on the cellular metabolism. Inter alia, signal transduction enzymes such as protein kinase C, tyrosine protein kinase and phosphatidylinositol 3-kinase are modulated (Agullo, G.; Gamet-payrastre, L.; Manenti, S.; Viala, C.; Remesy, C.; Chap, H.; Payrastre, B. Relationship between flavonoid structure and inhibition of phosphatidylinositol 3-kinase: a comparison with tyrosine kinase and protein kinase C inhibition. *Biochem Pharmacol* 53:1649-1657, (1997); Ferriola, P. C.; Cody, V.; Middleton, E. Protein kinase C inhibition by plant flavonoids. Kinetic mechanisms and structure activity relationship. *Biochem Pharmacol* 38: 1617-1624, (1989); Cushman, M.; Nagarathman, D.; Burg, D. L.; Geahlen, R. L. Synthesis and protein-tyrosine kinase inhibitory activity of flavonoids analogues. *J Meed Chem* 34: 798-806, (1991); Hagiwara, M.; Inoue, S.; Tanaka, T.; Nunoki, K.; Ito, M.; Hidaka, H. Differential effects of flavonoids as inhibitors of tyrosine protein kinases and serine/threonin protein kinases. *Biochem Pharmacol* 37: 2987-2992, (1988)), which downregulates inducible NO-synthase (Kobuchi, H.; Droy-Lefaix, M. T.; Christen, Y.; Packer, L. Ginkgo biloba extract (EGb761): inhibitory effect on nitric oxide production in the macrophage cell line RAW 264.7. *Biochem Pharmacol* 53: 897-903, (1997)) and which regulates the gene expression of, for example, interleukins and adhesion molecules (ICAM-1, VCAM-1) (Kobuchi, H.; Droy-Lefaix, M. T.; Christen, Y.; Packer, L. Ginkgo biloba extract (EGb761): inhibitory effect on nitric oxide production in the macrophage cell line RAW 264.7. *Biochem Pharmacol* 53:897-903, (1997); Wolle, J.; Hill, R. R.; Ferguson, E.; Devall, L. J.; Trivedi, B. K.; Newton, R. S.; Saxena, U. Selective inhibition of tumor necrosis factor-induced vascular cell adhesion molecule-1 gene expression by a novel flavonoid. Lack of effect on transcriptional factor NF-kB. *Atherioscler Thromb Vasc Biol* 16: 1501-1508, (1996)). It is proven that these effects have a positive action for preventing cardiovascular diseases, diabetes, various kinds of tumors and other chronic diseases (Bertuglia, S.; Malandrino, S.; Colantuoni, A. Effects of the natural flavonoid delphinidin on diabetic microangiopathy. *Arznei-Forsch/Drug Res* 45: 481-485, (1995); Griffiths, K.; Adlercreutz, H.; Boyle, P.; Denis, L.; Nicholson, R. I.; Morton, M. S. *Nutrition and Cancer Oxford*: Isis Medical Media, (1996);

Hertog, M. G. L.; Fesrens, E. J. M.; Hollman, P. C. K.; Katan, M. B.; Kromhout, D. Dietary antioxidant flavonoids and risk of coronary heart disease: the Zutphen elderly study. *The Lancet* 342: 1007-1011, (1993); Kapiotis, S.; Hermann, M.; Held, I.; Seelos, C.; Ehringer, H.; Gmeiner, B. M. Genistein, the dietary-derived angiogenesis inhibitor, prevents LDL oxidation and protects endothelial cells from damage by atherogenic LDL. *Arterioscler Thromb Vasc Biol* 17: 2868-74, (1997); Stampfer, M. J.; Hennekens, C. H.; Manson, J. E.; Colditz, G. A.; Rosner, B.; Willet, W. C. Vitamin E consumption and the risk of coronary disease in women. *New Engl J Med* 328:1444-1449, (1993); Tijburg, L. B. M.; Mattern, T.; Folts, J. D.; Weisgerber, U. M.; Katan, M. B. Tea flavonoids and cardiovascular diseases: a review. *Crit. Rev Food Sci Nutr* 37: 771-785, (1997); Kirk, E. A.; Sutherland, P.; Wang, S. A.; Chait, A.; LeBoeuf, R. C. Dietary isoflavones reduce plasma cholesterol and atherosclerosis in C57BL/6 mice but not LDL receptor-deficient mice. *J Nutr* 128: 954-9, (1998)). A series of curative compositions, health-promoting compositions or tonics whose action is based on their content of phenolic substances is therefore already being obtained from suitable plants (Gerritsen, M. E.; Carley, W. W.; Ranges, G. E.; Shen, C. P.; Phan, S. A.; Ligon, G. F.; Perry, C. A. Flavonoids inhibit cytokine-induced endothelial cell adhesion protein gene expression. *Am J Pathol* 147: 278-292, (1995); Lin, J. K.; Chen, Y. C.; Huang, Y. T.; Lin-Shiau, S. Y. Suppression of protein kinase C and nuclear oncogene expression as possible molecular mechanisms of cancer chemoprevention by apigenin and curcumin. *J Cell Biochem Suppl* 28-29:39-48, 1997; Zi, X.; Mukhtar, H.; Agarval, R. Novel cancer chemopreventive effects of a flavonoid antioxidant silymarin: inhibition of mRNA expression of an endogenous tumor promoter TNF alpha. *Biochem Biophys Res Comm* 239:334-339, 1997). It is also known that certain plant-derived foodstuffs or stimulants prepared from them have a positive effect on various diseases. Resveratrol, which occurs in white wine, but in particular in red wine (in addition to other components), for example, is active against cardiovascular diseases and cancer (Gehm, B. D.; McAndrews, J. M.; Chien, P.-Y.; Jameson, J. L. Resveratrol, a polyphenolic compound found in grapes and wine, is an agonist for estrogen receptor. *Proc Natl Acad Sci USA* 94: 14138-14143, (1997); Jang, M.; Cai, L.; Udeani, G. O.; Slowing, K. V.; Thomas, C. F.; Beecher, C. W. W.; Fong, H. H. S; Farnsworth, N. R.; Kinghorn, A. D.; Mehtha, R. G.; Moon, R. C., Pezzuto, J. M. Cancer chemopreventive activity of resveratrol, a natural product derived from grapes. *Science* 275: 218-220, (1997)). A similar effect is also found in substances such as catechin, epicatechin-3-gallate, epigallocatechin and epigallocatechin-3-gallate, which are found in the leaves of tea (*Camellia sinensis*). Beverages, in particular those made with unfermented tea leaves (green tea), are beneficial for health (Hu, G.; Han, C.; Chen, J. Inhibition of oncogene expression by green tea and (−)-epigallocatechin gallate in mice. *Nutr Cancer* 24: 203-209; (1995); Scholz, E; Bertram, B. *Camellia sinensis* (L.) O. Kuntze. Der Teestrauch [the tea shrub]. *Z. Phytotherapie* 17: 235-250, (1995); Yu, R.; Jiao, J. J.; Duh, J. L.; Gudehithlu, K.; Tan, T. H.; Kong, A. N. Activation of mitogen-activated protein kinases by green tea polyphenols: potential signaling pathways in the regulation of antioxidant responsive elements-mediated phase II enzyme gene expression. *Carcinigenesis* 18: 451-456, (1997); Jankun, J.; Selman, S. H.; Swiercz, R. Whydrinking green tea could prevent cancer. *Nature* 387: 561, (1997)). In addition, polymethoxylated flavones from citrus fruits also have a potential antitumor action (Chem, J.; Montanari, A. M.; Widmer, W. W. Two new polymethoxylated flavones, a class of compounds with potential anticancer activity, isolated from cold pressed dancy tangerine peel oil solids. *J Agric Food Chem* 45: 364-368, (1997)).

Acylcyclohexanediones such as prohexadione-calcium and trinexapac-ethyl (earlier name: cimectacarb) are employed as bioregulators for inhibiting longitudinal growth in plants. Their bioregulatory action is based on their blockage of the biosynthesis of gibberellins, which promote longitudinal growth. Owing to their structural relationship with 2-oxoglutaric acid, they inhibit certain dioxygenases which require 2-oxoglutaric acid as co-substrate (Rademacher, W, Biochemical effects of plant growth retardants, in: Plant Biochemical Regulators, Gausman, H W (ed.), Marcel Dekker, Inc., New York, pp. 169-200 (1991)). It is known that such compounds also engage in the phenol metabolism and can therefore cause inhibition of anthocyanin production in various kinds of plants (Rademacher, W et al., The mode of action of acylcyclohexanediones—a new type of growth retardant, in: Progress in Plant Growth Regulation, Karssen, C M, van Loon, L C, Vreugdenhil, D (eds.), Kluwer Academic Publishers, Dordrecht (1992)). Such effects on the balance of phenolic constituents are given as the cause of the side effect of prohexadione-calcium against fire blight (Rademacher, W et al., prohexadione-Ca—a new plant growth regulator for apple with interesting biochemical features, Poster presented at the 25th Annual Meeting of the Plant Growth Regulation Society of America, Jul. 7-10, 1998, Chicago). A. Lux-Endrich (PhD thesis at the Technical University Munich at Weihenstephan, 1998) found during her studies into the mechanism of action of prohexadione-calcium against fire blight that, in apple tissue cultures, prohexadione-calcium results in the content of phenolic substances being increased several times and that a series of phenols is found which is otherwise not present. It was also found during this study that exposure to prohexadione-calcium leads to relatively large amounts of luteoliflavan and eriodictyol in the shoot tissue of apples. Luteoliflavan does normally not occur in apple tissue, and eriodictyol occurs only in small amounts as an intermediate in the flavonoid metabolism. However, the expected flavonoids catechin and cyanidin were not detectable in the treated tissue, or found in considerably reduced amounts only (S. Römmelt et al., paper presented at the 8th International Workshop on Fire Blight, Kusadasi, Turkey, Oct. 12-15, 1998).

Figure 1:
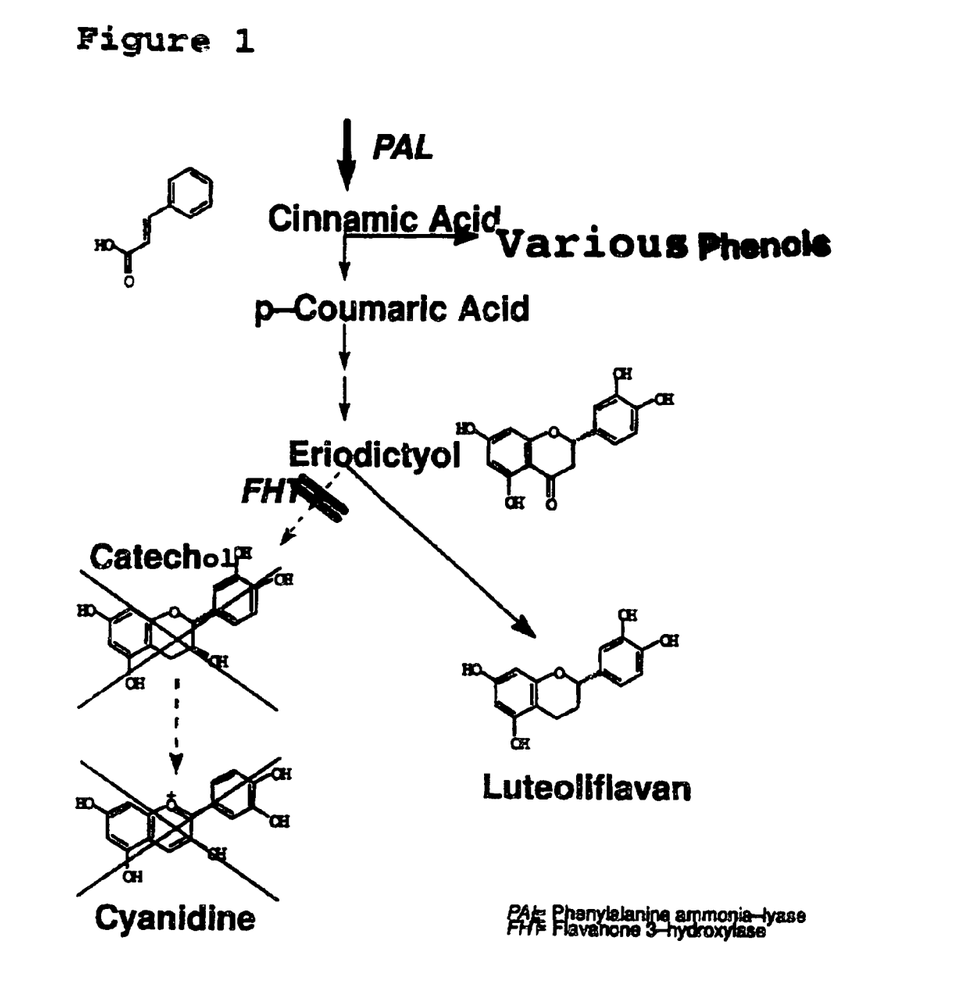
FIGS. 1-4. Illustration of Results.

It can be considered as proven that prohexadione-calcium, trinexapac-ethyl and other acylcyclohexanediones inhibit 2-oxoglutaric-acid-dependent hydroxylases which are of importance in the metabolism of phenolic substances. These hydroxylases are primarily chalcone synthetase (CHS) and flavanone 3-hydroxylase (F3H) (W. Heller and G. Forkmann, Biosynthesis, in: The Flavonoids, Harborne, J B (ed.), Chapman and Hall, New York, 1988). However, it cannot be excluded that acylcyclohexanediones also inhibit other 2-oxoglutaric-acid-dependent hydroxylases which are as yet unknown. Furthermore, it should be obvious that lack of catechin, cyanidin or other end products of flavonoid synthesis is registered by the plant and that the activity of the key enzyme phenylalanine ammonium-lyase (PAL) is increased by a feedback mechanism. However, since CHS and F3H are still being inhibited, these flavonoid end products cannot be formed, and the result is an increased production of luteoliflavan, eriodictyol and other phenols (FIG. 1).

It is an object of the present invention to provide an economic, simple method for increasing the content of flavonoids and phenolic compounds in plants and to improve their health-promoting properties.

We have found that this object is achieved, surprisingly, by treating the plants with the growth-regulating compounds from the group of the acylcyclohexanediones (I)

in particular with the compounds prohexadione-calcium (II)

and trihexapac-ethyl (III)

Treatment of the plants with the acylcyclohexanediones of the formula (I), prohexadione-calcium (II) and trinexapac-ethyl (III) allows the flavonoids eriodictyol, proanthocyanidines, which are substituted on the C-atom 3 by hydrogen, for example luteoforol, luteoliflavan, apigeniflavan and tricetiflavan, and homogeneous and heterogeneous oligomers and polymers of the above-mentioned, structurally related, substances to be formed in greater quantities.

Increased concentrations of the phenols hydroxycinnamic acid (p-coumaric acid, ferulic acid, sinapic acid), salicylic acid or umbelliferone, including the homogeneous and heterogeneous oligomers and polymers formed with them, can be identified after the compounds acylcyclohexanedione of the formula (I), prohexadione-calcium (II) and trihexapac-ethyl (III) have been applied to plants.

The concentration of the glycosides of the flavonoids, of the phenolic compounds, of the chalcones and of the stilbenes in the plants is also increased by treating the plants with the acylcyclohexanediones of the formula (I), prohexadione-calcium (II) and trinexapac-ethyl (III).

Also, prohexadione-calcium, trinexapac-ethyl and related compounds engage in other metabolic reactions where, as yet, it has only been possible to assume that 2-oxoglutarate-dependent dioxygenases are involved.

A further additional positive effect when obtaining preparations from higher plants with an improved curative, health-promoting or tonifying action is that, owing to the growth-regulatory action of prohexadione-calcium, trinexapac-ethyl or related acylcyclohexanediones, a concentration effect of the relevant constituents results in the biological material.

The method according to the invention for increasing the content of flavonoids and phenolic constituents by treating the plants with compounds from the group of the acylcyclohexanediones of the formula I, specifically prohexadione-calcium or trinexapac-ethyl, can be applied successfully to the following plants, but it is also possible successfully to treat plants which are not mentioned: grapevines, cherries, plums, sloes, blueberries, strawberries, citrus fruit (such as oranges, grapefruit), pawpaw, red cabbage, broccoli, Brussel sprouts, kale, carrots, parsley, celery/celeriac, onions, garlic, tea, coffee, cacao, maté, hops, soya, oilseed rape, oats, wheat, rye, Aronia melanocarpa and *Ginkgo biloba*.

Plants which have been treated with compounds from the group of the acylcyclohexanediones, specifically prohexadione-calcium or trihexapac-ethyl, in order to increase the content of flavonoids and phenolic compounds, or parts of these plants or products prepared from them (juices, infusions, extracts, fermentation products and fermentation residues) can be used for preparation of curative compositions, health-promoting compositions or tonics for humans and animals, and of cosmetics.

It is also possible to prepare, from the plants which have been treated in accordance with the invention, compositions wherein grapes of red grapevines are harvested and processed whose anthocyanin production has been prevented fully or partially by treatment with acylcyclohexanediones such as prohexadione-calcium or trinexapac-ethyl and which are therefore distinguished by a qualitatively and quantitatively increased content of flavonoids and other phenolic constituents.

Surprisingly, it has been found that the effect of a treatment with acylcyclohexanediones of the formula I, prohexadione-Ca or trihexapac-ethyl, causes the following to be observed in the plants, parts of these plants or products prepared from them (infusions, extracts, fermentation products, juices and the like):

(1) the antioxidative capacity in vitro (electron spin resonance (ESR), LDL oxidation, total antioxidant capacity, NO scavenging) is improved;
(2) a modulating effect on enzymes, especially signal transduction enzymes (protein kinase C, tyrosin protein kinase, phosphatidylinositol 3-kinase) is observed;
(3) a modulation of redox-sensitive transcriptional factors (NP-kB, AP-1) in endothelial cells, lymphocytes and smooth muscle cells is induced;
(4) the regulation of gene expression of target genes which are involved in the pathogenesis of inflammatory diseases (cytokines IL-1 and IL-8, macrophage chemoattractant protein 1 (MCP-1), adhesion factors ICAM-1 and VCAM-1) is modulated;
(5) an antiaggregatory action is induced;
(6) the cholesterol synthesis in the hepatocytes is inhibited;
(7) antiproliferative/antineoplastic effects are observed.

EXAMPLE 1

Increase of the Eriodictyol and Luteoliflavan Content in Young Apple Leaves Following Treatment with Prohexadione-Calcium Apple plants cv. "Weirouge" were grown under controlled-environment conditions and treated to runoff point with 250 ppm prohexadione-calcium (formulated as BAS 125 10 W=wettable granules, content 10%). At various points in time after the treatment, the youngest fully developed leaf was harvested from each individual shoot. The freeze-dried leaves which had been ground using a pestle and mortar were extracted with methanol. Flavonoids and related compounds in the concentrated extract were analyzed by HPLC. Separation was performed on Hypersil ODS (particle size 3 µm) on a 250×4 mm column. Elution was carried out at a flow rate of 0.5 ml per minute, and mixtures of formic acid (5% in water) and methanol, increased stepwise from a ratio of 95:5 to 10:90 (v/v) were used. Phenolic acids and flavonols were detected at 280 nm. Flavan-3-ols were determined by post-column derivatization with p-dimethylaminocinnamaldehyde at 640 nm. For methodological details, see Treutter et al. (1994), Journal of Chromatography A 667, 290-297.

The result is shown in the table which follows:

Leaves treated with prohexadione-calcium show a markedly increased eriodictyol concentration after 12 and 21 days.

|  | Treatment | | | |
|---|---|---|---|---|
|  | Eriodictyol [g/kg dry matter] | | Luteoliflavan [g/kg dry matter] | |
|  | 12 days after treatment | 21 days after treatment | 12 days after treatment | 21 days after treatment |
| Control | 0 | 1 | 0 | 70 |
| 250 ppm prohexadione-calcium | 17 | 27 | 0 | 34 |

EXAMPLE 2

Preparation of Sample Materials from Treated and Untreated Dornfelder Grapes

Vines cv. "Dornfelder" were treated twice at different points in time with the formulation BAS 125 10W, which contains prohexadione-calcium. 1000 g of prohexadione-calcium in 1000 l of spray mixture were applied per ha per treatment.

The 1st application was carried out at developmental stage 73 before the berries developed their color, and the 2nd application 10 days thereafter.

When harvested, the untreated and treated grapes showed a similar degree of ripeness. Untreated control: 69° Oechsle, acid: 7.3 g/l; treated control: 67° Oechsle, acid: 7.4 g/l.

Pigmentation was less pronounced in the treated grapes. As regards taste, no difference was observed.

The grapes were made into red wine by customary methods, i.e. the must was left to stand on the pulp for a prolonged period to improve pigment extraction.

After the wine which was free from cloudiness had been freeze-dried, approx. 2.5 g of a syrupy residue was obtained from 100 ml of untreated wine and approx. 2.1 g of syrupy residue from the wine from those vines which had been treated with prohexadione-calcium.

EXAMPLE 3

Inhibition of Cholesterol Biosynthesis in Primary Rat Hepatocyte Cultures by Prohexadione-Calcium Treated Dornfelder Wine Preparation of the Stock Solutions A quantity of the lyophilisate of the untreated and treated Dornfelder wines of between 10 and 20 mg was weighed exactly and treated with such an amount of DMSO that a stock solution of 10 mM total flavonoids resulted. These stock solutions were used for preparing dilutions in the culture medium immediately prior to the beginning of the test. The dilutions were done in 10-fold dilution steps of between $10^{-4}$ and $10^{-8}$ M.

Preparation of the Hepatocyte Cultures

Primary hepatocytes were obtained from the livers of Sprague-Dawley rats (240-290 g) by means of collagenase perfusion (Gebhardt et al., Arzneimittel-Forschung/Drug Res. 41: 800-804 (1991) 1990). They were cultured in collagen-coated Petri dishes (6-well plates, Greiner, Nürtingen) at a cell density of 125,000 cells/cm$^2$ in Williams medium E supplemented with 10% calf serum. More detailed information, in particular on the culture medium, are found in Gebhardt et al., Cell Biol. Toxicol. 6: 369-372 (1990) and Mewes et al., Cancer Res. 53: 5135-5142 (1993). After 2 h, the cultures were transferred to serum-free medium supplemented with 0.1 µm insulin. After a further 20 h, they were employed in the experiments. The test substances were each tested in three independent cultures of 2-3 rats.

Incubation of the Liver Cell Cultures with the Test Substances

To demonstrate that cholesterol biosynthesis is influenced by the test substances, the hepatocyte cultures were maintained for 22 h in total. Then, they were incubated for 2 h in serum-free Williams medium E supplemented with $^{14}$C-acetate (tracer quantities only) with the test substances at the concentrations indicated. Each test series included a control. The methodology is described in detail by Gebhardt (1991) and Gebhardt, Lipids 28: 613-619 (1993). The tracer quantities of $^{14}$C-acetate exchange rapidly with the intracellular acetyl-CoA pool and therefore allow the incorporation of $^{14}$C-acetate into the sterol fraction, >90% of which consists of cholesterol, to be detected without interference (Gebhardt, 1993).

Analysis of the Effect on Cholesterol Biosynthesis

The incorporation of $^{14}$C-acetate into the sterol fraction (non-hydrolyzable lipids) was measured using the method of Gebhardt (1991). If the extraction is carried out by means of Extrelut® columns (Merck, Darmstadt), over 95% of the $^{14}$C-acetate (and other low-molecular-weight metabolites formed therefrom in minor quantities) is removed. This test can provide comparative information on the relative synthesis rate of cholesterol and precursor sterols under the influence of test substances (Gebhardt, 1993).

Visual and Microbial Quality Checks of the Hepatocyte Cultures

Before and after the test incubation, all cultures used were checked visually under the microscope for contamination with microorganisms and for the integrity of the cell monolayer. In none of the samples was a noticeable change in cell morphology observed (in particular at the higher concentrations). This largely rules out the possibility that the test results were influenced by cytotoxic effects of the test substances.

The sterility tests, which were carried out routinely in all cultures, did not suggest any contamination with microorganisms.

Results

The untreated Dornfelder wine showed no effects whatsoever on cholesterol biosynthesis. In contrast, the cholesterol synthesis was inhibited significantly by samples of wine which originated from prohexadione-calcium-treated vines.

At a concentration of $10^{-5}$ M, the inhibitory effect was approx. 60% and at $10^{-4}$ M almost 100%.

EXAMPLE 4

Effect of Prohexadione-Ca-Treated Wine Extract (P—Ca) on the Destruction of Tumor Cells Confluent murine leukemia cells (RAW 264.7) and normal macrophages from the peritoneum of rats were cultivated in DMEM medium supplemented with fetal calf serum. Extracts of untreated and prohexadione-Ca-treated wine were added to the culture medium, up to a dosage of 200 µg/ml. In parallel experiments, 10, 25 and 50 µg/ml wine extract were incubated together with 100 µM $H_2O_2$.

Figure 2:
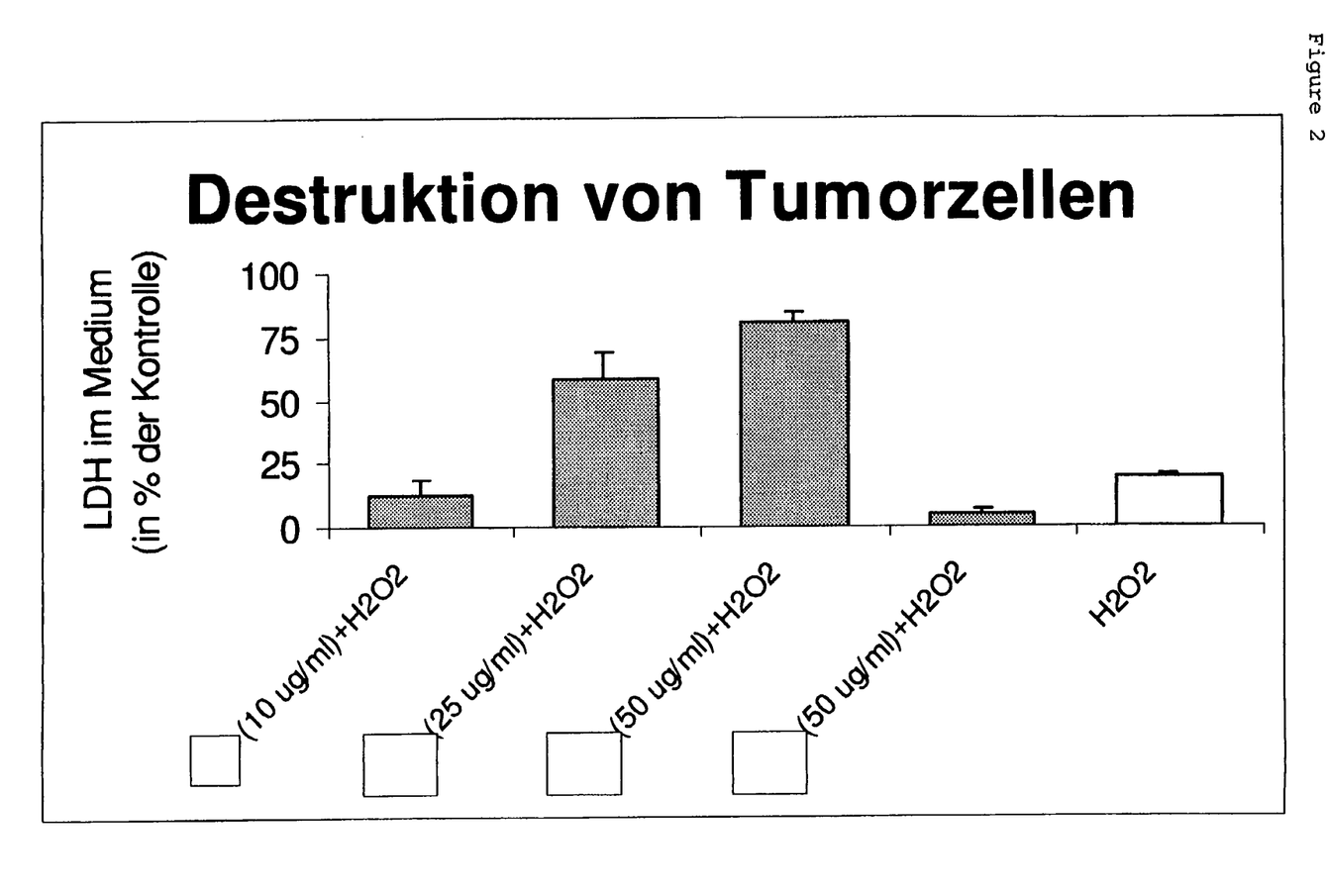
Figure 3:
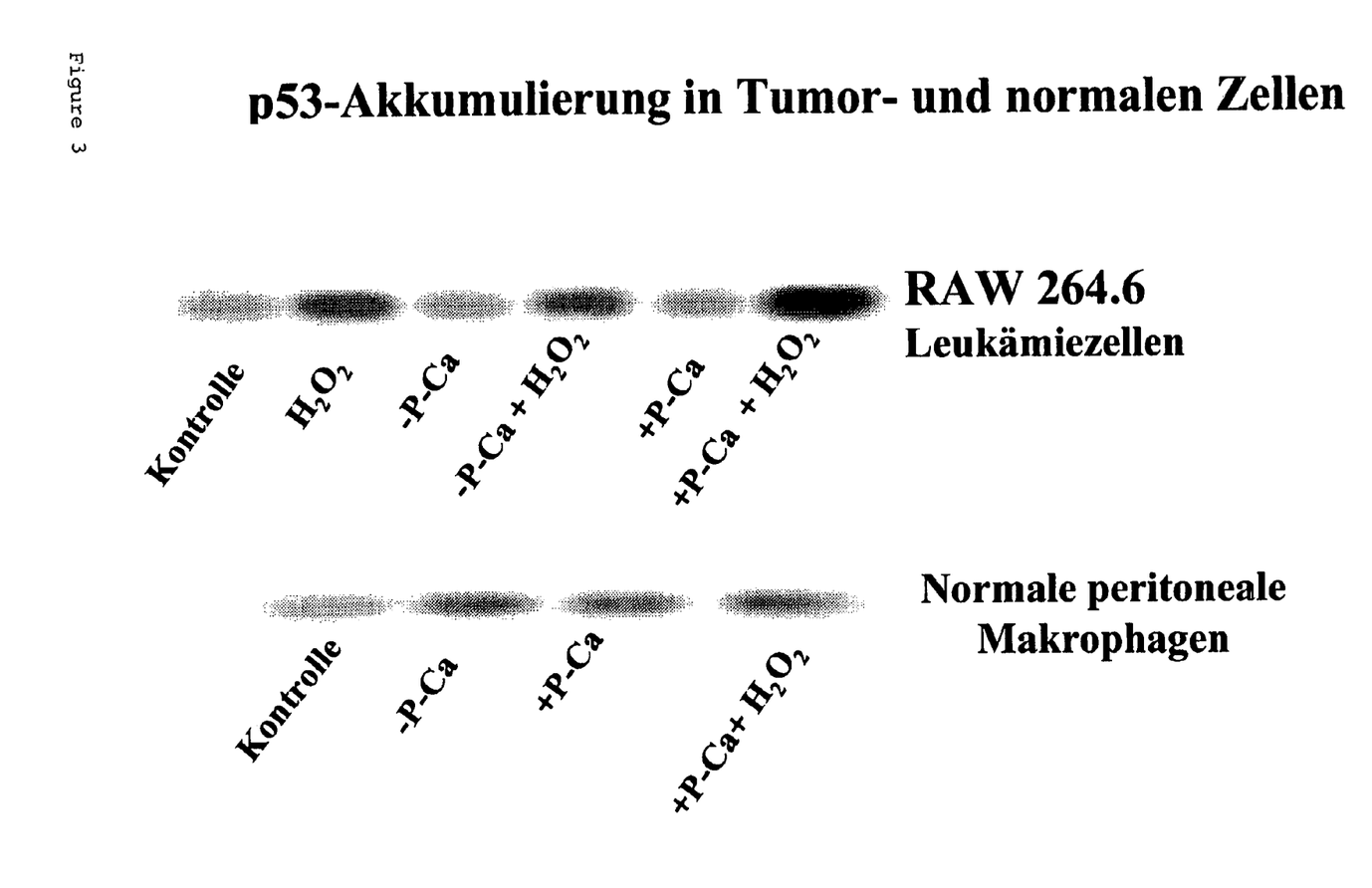

Wine extract of wine which had been treated with prohexadione-Ca per se up to a dosage of 200 µg/ml had no cytotoxic effect on the cell cultures examined. However, after addition of $H_2O_2$ prohexadione-Ca-treated extract increased cell death of the tumor cells (RAW 264.7) in a dose-dependent manner. This is documented in FIG. 2 by the increase of the cytosolic enzyme lactate dehydrogenase (LDH) in the culture medium. In nontransformed macrophages, there was no increase of the cytotoxic effect of $H_2O_2$. In the tumor cell line, there was an accumulation of the protein from the tumor suppressor gene p53 in the cytoplasm, see FIG. 3.

Prohexadione-treated wine extract increases $H_2O_2$-induced cytotoxicity of leukemia cells but is ineffective in normal macrophages. This tumor-cell-specific effect is also observed in the case of cytostatics which act via increased oxidative stress (for example anthracyclines). The mechanism of prohexadione-Ca-treated wine extract is p53-dependent.

EXAMPLE 5

Effect of Prohexadione-Ca-Treated Wine Extract on NF-κB Activation in Endothelial Cells The experiment was carried out using cocultures of macrophages (RAW 264.7) and endothelial cells (ECV 304). The culture medium of the endothelial cells was admixed with human LDL (low-density lipoproteins) and resting or interferon-γ (IFN-γ)-activated (10 U/ml) macrophages. After 16 h of incubation, the nuclear protein fraction was separated off and DNA binding (activation) of the redox-sensitive transcription factor NF-κB was determined in an electrophoretic mobility shift assay.

Figure 4:
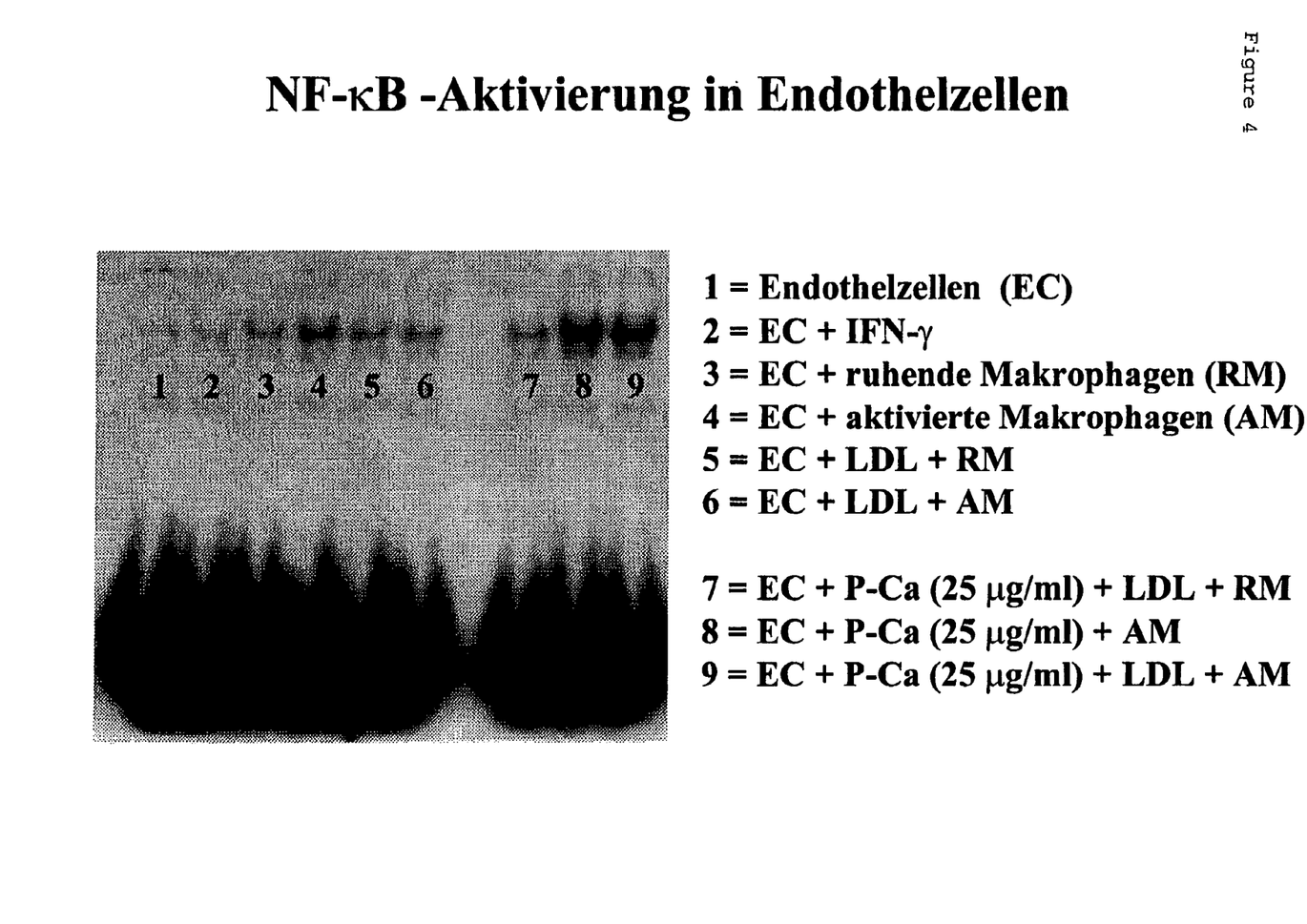

The basal content in the resting endothelial cells was typically low, see FIG. 4. Addition of LDL resulted in activation of NF-κB, which was higher in activated macrophages than in resting macrophages. This corresponds to a physiological oxidation of LDL during atherogenesis. In all cases, incubation with prohexadione-Ca-treated wine extract resulted in an increased NF-κB activation.

The cell culture model used is highly suitable for describing the pathophysiological/inflammatory conditions in the early phase of atherosclerosis. NF-κB activation is enhanced by the prohexadione-Ca-treated wine extract. This is equivalent to the action of a biological response modifier; i.e. the cellular response to a pathophysiological signal is enhanced in the positive sense.

We claim:
1. A method of increasing and qualitatively modifying the content of flavonoids and phenolic constituents in a plant selected from grapevines and hops, which comprises treating the plant with an acylcyclohexanedione of the formula I where R is hydrogen or $C_1$-$C_6$-alkyl and R' is $C_1$-$C_6$-alkyl or $C_3$-$C_6$-cycloalkyl, or with a suitable salt of I, thereby giving the plant an increased and qualitatively modified content of flavonoids and phenolic constituents compared to an untreated plant.

2. A method as claimed in claim 1, wherein the plant is treated with an acylcyclohexadione of the formula II and/or the formula III 3. A method as claimed in claim 1, wherein the content of flavonoids and phenolic constituents of grapevines is increased and qualitatively modified.

4. A method as claimed in claim 1, wherein the content of flavonoids with an unsubstituted C atom in the 3-position, and of the oligomers and polymers of these flavonoids, is increased.

5. A method as claimed in claim 1, wherein the plant is a grapevine.

6. A method for producing a plant preparation with an increased and qualitatively modified content of flavonoids and phenolic constituents, which method comprises
   (1) treating a plant selected from grapevines and hops, with an acylcyclohexanedione of formula I where R is hydrogen or $C_1$-$C_6$-alkyl and R' is $C_1$-$C_6$-alkyl or $C_3$-$C_6$-cycloalkyl, or with a suitable salt of I; and
   (2) harvesting and processing the plant or parts of the plant to obtain a plant preparation which has an increased and qualitatively modified content of flavonoids and phenolic constituents.

7. The method as claimed in claim 6, wherein the plant is treated in step (1) with an acylcyclohexanedione of formula II and/or formula III 8. The method as claimed in claim 6, where a plant preparation with an increased content of flavonoids with an unsubstituted C-atom in the 3-position, and of the oligomers and polymers of these flavonoids, is obtained.

9. The method as claimed in claim 6, wherein the plant is a grapevine.

10. A wine grape extract, wine grape juice, wine or wine grape press cake comprising flavonoids and other phenolic constituents obtained from grapes of a grapevine plant of a red grapevine variety, the grapevine plant previously having been treated with at least one acylcyclohexanedione of the formula I where R is hydrogen or $C_1$-$C_6$-alkyl and R' is $C_1$-$C_6$-alkyl or $C_3$-$C_6$-cycloalkyl, or with a suitable salt of I, and wherein, due to the treatment of the grapevine plant with the acylcyclohexanedione of formula I, the content of at least one of luteoforol, luteoliflavan, apogeniflavan, tricetiflavan, or oligomers or polymers thereof, is increased.

11. A composition or tonic health-promoting composition or tonic for humans and animals, or a cosmetic comprising a hop plant or a part of the plant or a product prepared with the plant selected from juices, extracts, fermentation products and fermentation residues, wherein said plant has been treated with the acylcyclohexanedione of the formula I where R is hydrogen or $C_1$-$C_6$-alkyl and R' is $C_1$-$C_6$-alkyl or $C_3$-$C_6$-cycloalkyl, or with a suitable salt of I.

12. The composition or tonic as claimed in claim 11, wherein, due to the treatment of said hop plant with the acylcyclohexanedione of formula I, the content of flavonoids with an unsubstituted C-atom in the 3-position, or oligomers or polymers thereof, is increased.

13. The composition or tonic as claimed in claim 11, wherein, due to the treatment of said hop plant with the acylcyclohexanedione of formula I, the content of at least one of luteoforol, luteoliflavan, apogeniflavan, tricetiflavan, or oligomers or polymers thereof, is increased.

* * * * *